United States Patent

Koshihara et al.

[11] Patent Number: 5,903,004
[45] Date of Patent: May 11, 1999

[54] ENERGY DISPERSIVE X-RAY ANALYZER

[75] Inventors: Shunsuke Koshihara; Mitsugu Sato; Naomasa Suzuki, all of Hitachinaka, Japan

[73] Assignees: Hitachi, Ltd., Tokyo; Hitachi Instruments Engineering Co., Ltd., Hitachinaka, both of Japan

[21] Appl. No.: 08/911,186

[22] Filed: Aug. 14, 1997

Related U.S. Application Data

[63] Continuation-in-part of application No. 08/560,162, Nov. 20, 1995, abandoned.

[30] Foreign Application Priority Data

Nov. 25, 1994 [JP] Japan ................................. 6-291506

[51] Int. Cl.$^6$ ................................................. H01J 37/244
[52] U.S. Cl. ......................... 250/310; 250/397; 250/399; 250/505.1
[58] Field of Search ...................... 250/310, 397, 250/399, 505.1

[56] References Cited

U.S. PATENT DOCUMENTS

| | | | |
|---|---|---|---|
| 3,327,112 | 6/1967 | Akahori | 250/505.1 |
| 3,543,384 | 12/1970 | Hansen | 250/505.1 |
| 3,670,395 | 6/1972 | Abe et al. | 250/505.1 |
| 4,280,049 | 7/1981 | Werner et al. | 250/310 |
| 4,803,369 | 2/1989 | Otaka | 250/505.1 |
| 4,855,596 | 8/1989 | Gruen et al. | 250/310 |
| 4,910,399 | 3/1990 | Taira et al. | 250/310 |
| 5,065,020 | 11/1991 | Kanda | 250/310 |
| 5,266,802 | 11/1993 | Kasai | 250/310 |
| 5,289,005 | 2/1994 | Naruse et al. | 250/310 |

FOREIGN PATENT DOCUMENTS 0 966 717  8/1964  United Kingdom .

*Primary Examiner*—Bruce Anderson
*Attorney, Agent, or Firm*—Kenyon & Kenyon

[57] ABSTRACT

In an electron microscope employing an X-ray spectrometer according to the present invention, a collimator is provided in a head portion of the X-ray spectrometer and a part of the collimator is arranged in a leakage magnetic field of an objective lens included in the electron microscope, whereby the orbits of the scattering electrons are curved and hence the scattering electrons are prevented from colliding with the X-ray spectrometer to dissolve the background noises in the X-ray spectrum

11 Claims, 4 Drawing Sheets

ENERGY DISPERSIVE X-RAY ANALYZER

This application is a continuation-in-part of application Ser. No. 08/560,162 filed Nov. 20, 1995, now abandoned.

BACKGROUND OF THE INVENTION

The present invention relates in general to an energy dispersive X-ray analyzer, and more particularly to an energy dispersive X-ray analyzer which is capable of detecting the X-rays at high sensitivity without influencing the resolution of a system even when mounted to a high resolution scanning electron microscope having an objective lens of an inlens type or an objective lens of a magnetic field leakage type attached thereto, and also which is suitable for performing the high precision X-ray analysis.

In order to perform the high precision X-ray analysis in an energy dispersive X-ray analyzer (hereinafter referred to as "an EDX" for short, when applicable) employing an energy dispersion X-ray spectrometer, such as a silicon semiconductor detectors it is necessary to detect the X-rays which are emitted from a sample at high sensitivity and also to remove the scattering electrons (the reflected electrons) which are emitted attendantly from the sample due to the collision of the incident electron beams with the sample. Those reflected electrons become the background noises in the X-ray spectrum and also influence on the precision or the like in the quantitative analysis.

As shown in FIG. 1, in a detector included in a conventional EDX, in order to remove the scattering electrons 10 which pass, together with the X-rays 14, into an EDX device 12 as an X-ray spectrometer from a sample 7, a ring-like permanent magnet 17 is provided as an electron trap in the head portion of the EDX device 12 and the orbits of the scattering electrons 10 are curved by the magnetic field which is generated by that permanent magnet, thereby preventing the scattering electrons from entering into the EDX device.

In order to perform the high resolution observation with respect to the sample, the scanning electron microscope of a system in which the sample is arranged in the magnetic field generated by the objective lens (the inlens system or the magnetic field leakage system) is often used. However, in such a scanning electron microscope, since the sample is arranged in the magnetic field of the objective lens, if the EDX spectrometer which has the permanent magnet as the electron trap in the head portion of the X-ray spectrometer is brought close to the vicinity of the samples the magnetic field of the objective lens is disturbed by the magnetic field which is generated from the permanent magnet provided in the head portion of the X-ray spectrometers and hence the high resolution observation can not be performed. This is a problem inherent in the prior art. As a result, in such a high resolution scanning electron microscopes the EDX spectrometer can not be brought close to the sample, and hence the high sensitivity X-ray analysis and the high resolution observation can not be compatible with each other. This is another problem inherent in the prior art.

SUMMARY OF THE INVENTION

The present invention was made in order to solve the above-mentioned problems inherent in the prior art, and hence it is an object of the present invention to provide an energy dispersive X-ray analyzer which is capable of performing the X-ray analysis at high sensitivity without harming the lens performance (the resolution) of the scanning electron microscope even when combined with a scanning electron microscope having an inlens type objective lens or a magnetic field leakage type objective lens.

In order to attain the above-mentioned objects the present invention employs an EDX spectrometer in which a cylindrical collimator made of a non-magnetic material, such as aluminium, which does not influence the magnetic field generated by an objective lens is mounted to the head portion of an X-ray spectrometer. In this connection, a part of or the whole collimator is arranged in the magnetic field of the objective lens and the orbits of the scattering electrons are curved by the magnetic field of the objective lens, thereby preventing the scattering electrons from entering into the X-ray detector.

In additions an irregular structures that is structure, is provided on an inner wall of an X-ray passing hole of the collimator, whereby even if the scattering electrons, the orbits of which have been curved by the magnetic field of the objective lens, collide with the inner wall of the X-ray passing hole of the collimators the electrons which are generated due to the collision of the scattering electrons with the inner wall of the collimator is prevented from entering into the X-ray detection unit. The irregular structure may be either formed by threading the inner surface of the collimator or formed by roughening the inner surface thereof. It is sufficient that a height of the irregularity is about 0.1 mm.

In additions in order to reduce the amount of electrons which have been generated when the scattering electrons collide with the inner wall of the X-ray passing hole of the collimator, material (such as carbon) from which only a small number of electrons are generated due to the collision is applied to the inner wall of the X-ray passing hole of the collimator, or the collimator itself is made of a material, such as aluminium, from which only a small number of electrons are generated due to the collision.

Further, in order to prevent the scattering electrons from entering into the EDX device as much as possible, the size of the inlet port for the X-rays of the collimator is made narrower than that of the outlet port, i.e., the side in which the EDX device is arranged.

By virtue of the above-mentioned arrangement, the scattering electrons which have been generated from the sample by the irradiation of the electron beams are curved with the orbits thereof by the magnetic field of the objective lens and hence are prevented from entering into the EDX spectrometer. Even if the scattering electrons, the orbits of which have been curved by the magnetic field of the objective lens, collide with the inner wall of the X-ray passing hole of the collimator, since the inner wall of the X-ray passing hole of the collimator is made of the material from which only a small number of secondary electrons are generated due to the collision of the scattering electrons with the inner wall of the collimator, the number of secondary electrons which are generated from the X-ray passing hole due to the collision of the scattering electrons is reduced with every repetition of the collision. In addition, since the inner wall of the X-ray passing hole of the collimator has the irregular structure, even if the secondary electrons are generated by the collision of the scattering electrons with the inner wall of the X-ray passing hole of the collimator, those secondary electrons do not enter into the X-ray detector because they are interrupted by the irregular structure of the inner wall of the X-ray passing hole.

On the other hand, since the X-rays which have been generated from the sample go straight on irrespective of the presence of the magnetic field of the objective lens, the X-rays thus generated are detected by the EDX spectrometer. Thus, according to the present invention, even when the X-ray spectrometer is mounted in the scanning electron microscope in which the sample is arranged in the magnetic field of the objective lens, the X-ray analysis can be performed at high sensitivity without influencing the resolution of the scanning electron microscope.

In addition, by making the size of the inlet port for the X-rays of the collimator narrow it is possible that the scattering electrons hardly enter into the X-ray detector. By adopting this structure, since a large EDX device can be employed the efficiency of detecting the X-rays can be further improved as compared with the case where the minor diameter of the cylindrical collimator is simply made narrow. Further, this structure has the shape which is suitable for arranging the collimator in the leakage magnetic field generated by the objective lens without being interrupted by the objective lens.

Furthermore, the collimator is made of a material having a small transmission factor for the X-rays, whereby it is possible to prevent the generation of the secondary X-rays which will be excited and generated by applying the X-rays to the outer wall of the collimator. In additions it is also possible to prevent the generation of the X-rays which will be excited and generated due to the collision of the scattering electrons with the collimator. Since when the collimator is sharpened as in the present invention, the much amount of scattering electrons will collide with the outer wall of the collimator, the above-mentioned structure can be said to be a most effective structure.

DETAILED DESCRIPTION

Figure 1:
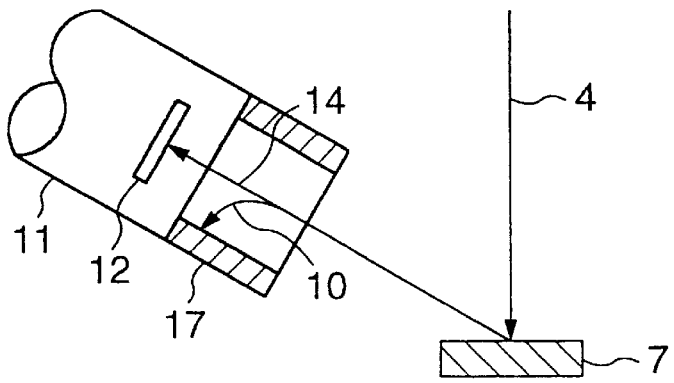
FIG. 1 is a schematic view showing a structure of a conventional EDX spectrometer.
Figure 2:
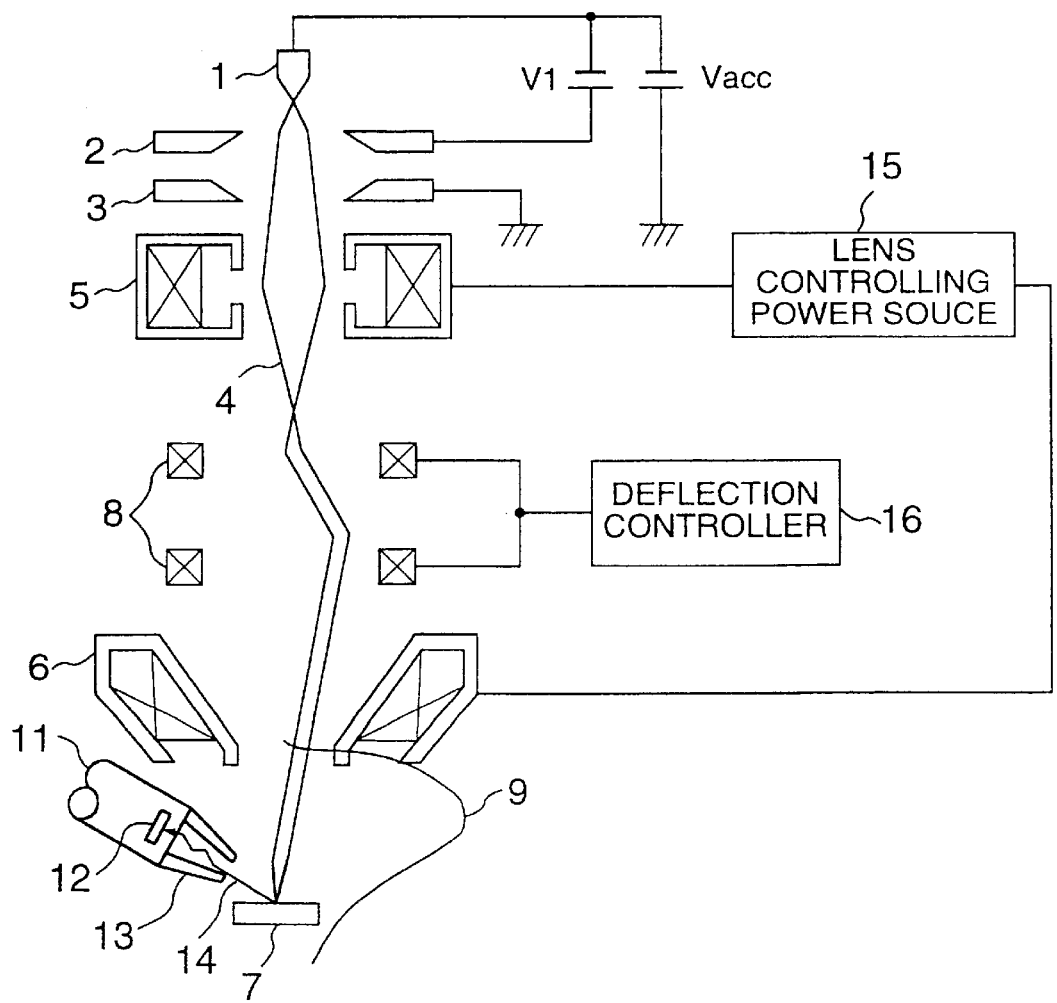
FIG. 2 is a schematic cross sectional views partly in block diagram, showing an arrangement of an embodiment of the present invention.

FIG. 2 is a schematic cross sectional view, partly in block diagram, showing an arrangement of an embodiment of the present invention. Incident electron beams 4, which have been emitted from a cathode 1 by applying a voltage V1 across the cathode 1 and a first anode 2, are accelerated by a voltage Vacc applied to a second anode 3 to move into the subsequent lens system. Those incident electron beams 4 are concentrated as a small spot on a surface of a sample 7 by the function of both a condenser lens 5 and an objective lens 6 which are controlled by a lens controlling power source 15 and then the sample is scanned in a two-dimensional manner with the electron beams thus concentrated through the function of two stage deflecting coils 8. A scanning signal of the deflecting coils 8 is controlled by a deflection controller 16 in accordance with the observation magnification. A magnetic field 9 of the objective coil 6 is generated on the sample side and hence the sample 7 is arranged in the magnetic field of the objective lens.

An energy dispersive X-ray (EDX) detector 11 includes an EDX device 12 and a collimator 13 which is arranged in the front of the EDX device 12. The collimator 13 is a cylindrical structure which is made of aluminium, for example, as a non-magnetic material. In this connection, a screw with about 0.1 mm height is threaded in the inner surface of the collimator 13. The EDX spectrometer 11 is arranged in such a way that the collimator 13 thereof is located in the magnetic field 9 generated by the objective lens 6.

Figure 3:
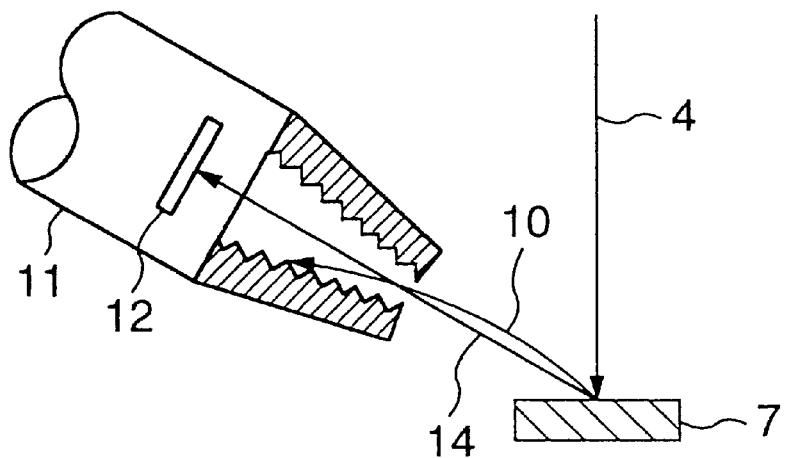
FIG. 3 is a schematic cross sectional view showing a structure of a collimator portion.

The X-rays 14 which have been emitted from the sample 14 pass through an X-ray passing hole of the collimator 13 and then are detected by the EDX device 12 provided in the EDX spectrometer 11. On the other hand, scattering electrons 10 which have been emitted from the sample 7 are, as shown in FIG. 3, curved with the orbits thereof by the magnetic field 9 of the objective lens 6 and hence can not pass through the X-ray passing hole of the collimator to collide with the inner wall of the collimator 13. The scattering electrons which have collided with the inner wall of the collimator 13 serve to generate the secondary electrons from the collision surface of the inner wall of the collimator, but can not move towards the EDX device 12 since the inner wall of the collimator has the irregular structure. In addition, since the surface of the inner wall is made of a material from which the secondary electrons are hardly generated due to the collision of the scattering electrons 10 with the inner wall of the collimator, the possibility that the scattering electrons 10 enter into the EDX device 12 becomes very small due to the mutually potentiating effect of that material and the above-mentioned irregular structure.

In addition, by making the collimator 13 of a material having a small transmission factor for the X-rays such as tungsten or tantalum, it is possible to prevent the generation of the secondary X-rays which will be excited and generated by applying the X-rays to the outer wall of the collimator 13. In addition, it is also possible to prevent the generation of the X-rays which will be excited and generated by the collision of the scattering electrons with the collimator 13. In particular, since when the collimator 13 is sharpened as in the present invention, most of electrons collide with the outer wall of the collimator, this structure is considered a most effective structure.

In addition, this structure is effective for measures against secondary X-rays. The reasons for this are explained with reference to FIG. 5.

Figure 5:
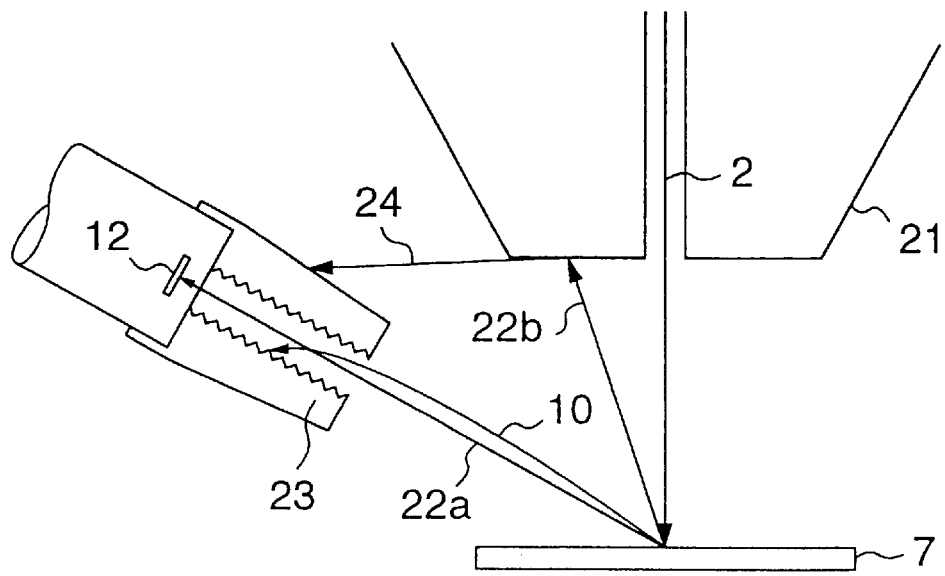
FIG. 5 shows how secondary X-rays are prevented from entering into a detector.

In FIG. 5, incident electron beams 2 which have gone through an objective lens 21 are irradiated onto a sample, so that X-rays 22a, 22b and reflection electrons 10 are emitted. The X-rays 22a are detected by EDX element 12. The reflection electrons 10 are prevented from entering into the EDX element 12 due to a magnetic deflection action of the objective lens 21 and the irregular structure, that is structure formed on an inner wall of collimator 23.

Figure 6:
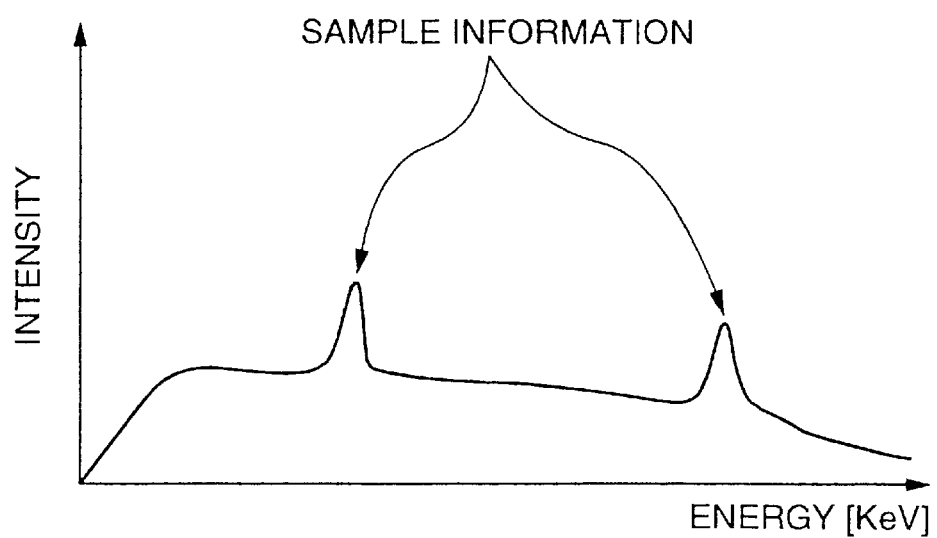
FIG. 6 shows an X-ray characteristic obtained in composition analysis of a sample according to an energy dispersion method in the structure of FIG. 5.

When a composition analysis of a sample is carried out according to an energy dispersion method under a structure shown in FIG. 5, an X-ray characteristic shown in FIG. 6 is obtained.

According to the composition analysis of a sample according to the energy dispersion method, elements included in the sample can be specified on the basis of the differences of spectra which are obtained according to the elements included in the sample.

Figure 7:
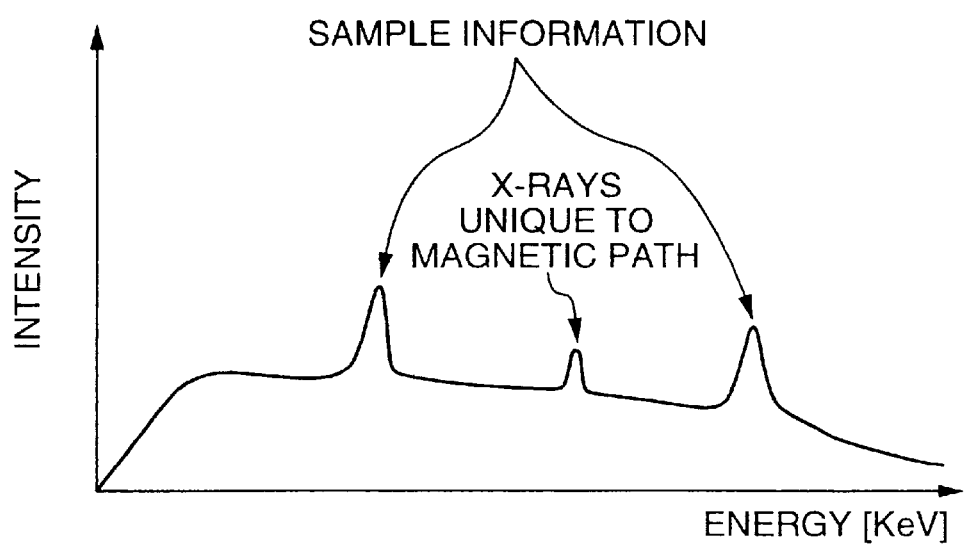
FIG. 7 shows an X-ray characteristic obtained when secondary X-rays are detected by an EDX element.

However, when the X-rays 22b emitted from the sample collide with an other member, in the preferred embodiment, it is the objective lens 21, as a result, X-rays 24 (hereinafter, it is called secondary X-rays) are emitted. The secondary X-rays have characteristics of elements of the other member. When the secondary X-rays collide with the EDX element 12, as shown in FIG. 7, X-rays which have no relationship with the elements of the sample, but are unique to the member forming the objective lens 21, are often detected.

In addition, secondary X-rays which are excited by the collision of X-rays emitted from the sample with the objective lens 21, and so forth, are present.

According to the embodiment shown in FIG. 5, when the composition analysis of a sample according to the energy dispersion method is carried out, in order to remove the influence of the X-rays emitted from the member which have no relationship with the sample, the collimator 23 is formed with material such as tantalum through which the X-rays are scarcely transmitted, so that detection precision can be improved.

Figure 8:
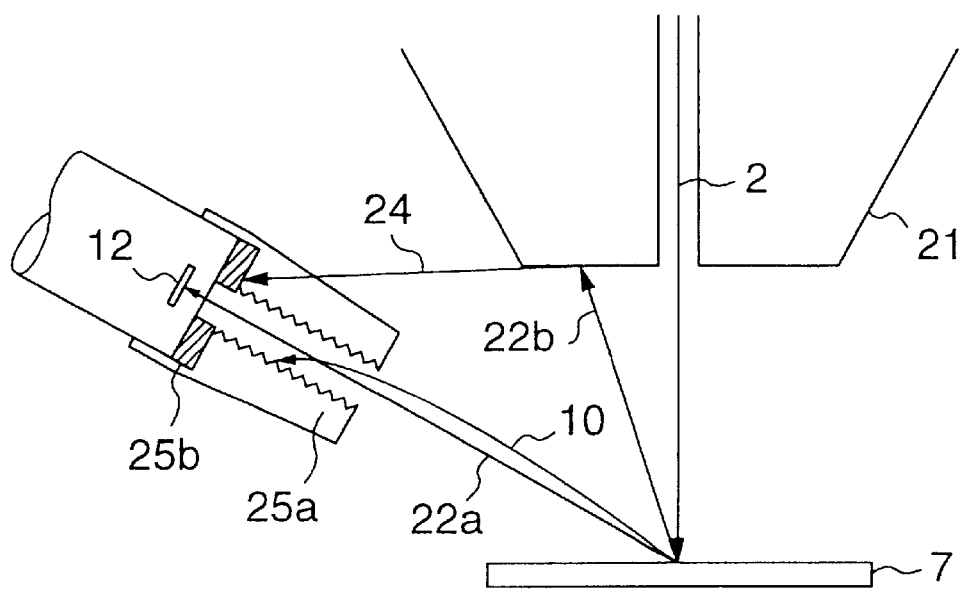
FIG. 8 shows another embodiment according to the present invention.

FIG. 8 shows another application of a collimator formed with the material through which the X-rays are scarcely transmitted.

The collimator shown in FIG. 8 has a first portion 25a formed with a non-magnetic material and a second portion 25b formed with the material through which the X-rays are scarcely transmitted. For example, the second portion 25b can be formed in a disk shape having the hole in a center thereof.

In general, since tantalum has a physical nature that is hard and fragile, it is not suitable for forming an irregular structure on an inner wall of a collimator, as already stated, or for processing for sharpening a head of the collimator that is explained afterward. Further, tantalum is generally expensive in comparison with aluminum which is used as a non-magnetic material in the preferred embodiment according to the present invention.

Further conditions required of the second portion 25b, if the X-rays emitted from materials other than the sample are prevented from entering into the EDX element 12 can also be satisfied. The functions required are different from those required for a collimator itself which is mainly formed in order to prevent the entrance of the reflection electrons. Accordingly, it is required that the second portion is formed so that at least the entrance of the secondary X-rays into the EDX element can be decreased.

In the preferred embodiment, in view of the conditions mentioned above, the collimator is formed with at least two materials one of which is a non-magnetic material and the other is a material which has at least less transmission factor of the X-rays than the non-magnetic material, so that detection efficiency due to the secondary X-rays can be prevented from decreasing and the processing of the collimator can be easily performed.

Further, in the preferred embodiments shown in FIGS. 5 and 8, since the secondary X-rays are mainly emitted by the collision of the X-rays 22b with the objective lens 21, the tantalum and so forth can be provided so as to insulate the interval between the objective lens 21 and the EDX element 12. Also, the tantalum can be attached to the objective lens 21 so that the generation of the secondary X-rays themselves can be prevented.

In either cases, it is enough for the tantalum and so forth that it can be formed in a sheet shape, so that it can be easily processed.

As the material through which the X-rays scarcely transmit, other than the tantalum (Ta), tungsten (W), gold (Au), platinum (Pt), lead (Pb), and so forth, can be mentioned. Gold, platinum and lead are easily processed, and tantalum and tungsten are superior to suppress the transmission of X-rays.

Figure 4:
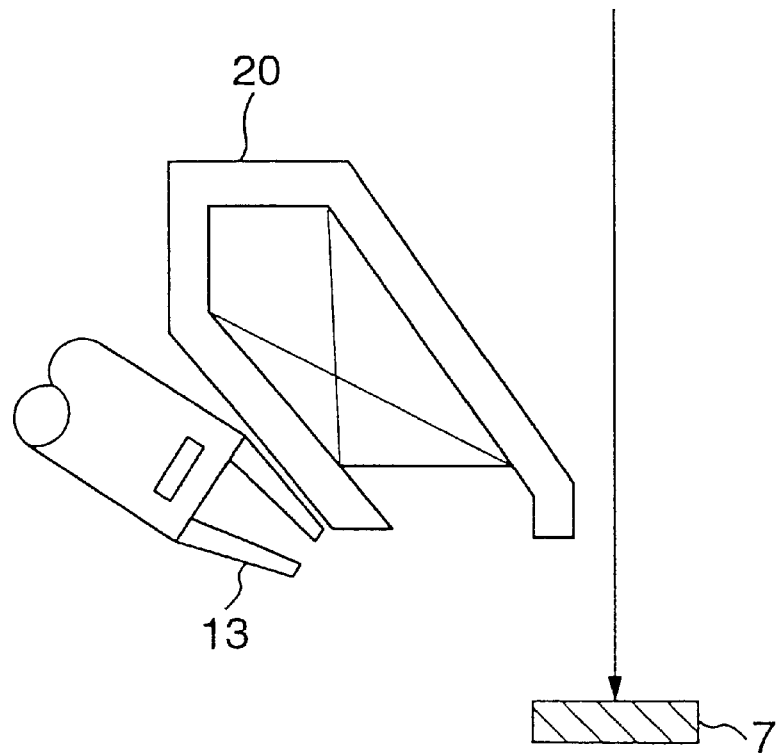
FIG. 4 is a schematic view showing an arrangement of a collimator of the present invention.

Since the collimator 13 is sharpened towards the sample as shown in FIG. 4 in the present inventions the collimator 13 can be readily brought close up to the leakage magnetic field of the objective lens 20 without being prevented by the objective lens 20. In addition, by sharpening the collimator 13, the inlet port for the X-rays is made narrower than the outlet port for the X-rays. In other words, it is possible to reduce the entrance of the scattering electrons into the EDX device 12. This structurally necessary condition is different in the following point from the style in which the minor diameter of the cylindrical collimator is simply narrowed to form a narrow cylinder.

That is, there is obtained an effect in which by sharpening the collimator 13, not only the inlet port of the collimator 13 can be narrowed, but also a large EDX device 12 can be employed. In general, the X-rays which have been obtained by applying the incident electron beams 4 to the sample 7 are emitted radially with the irradiation point of the incident electron beams on the sample as the center. In other words, if the whole minor diameter of the collimator is simply narrowed to intend to obtain the same inlet diameter as that of the collimator of the present invention, the detection efficiency is further reduced as compared with the present invention by the amount of X-rays which collide with the inner wall of the collimator between the inlet port of the collimator and the EDX device.

As described above, by sharpening the collimator, the collimator can be readily arranged in the leakage magnetic field of the objective lens, and also it is possible to reduce the entrance of the reflected electrons into the collimator.

Incidentally, in the case where both the efficiency of preventing the entrance of the scattering electrons into the collimator 13 and the efficiency of detecting the X-rays are taken into consideration, if the inner wall of the collimator 13 is formed along the straight line connecting the irradiation point of the incident electron beams on the sample 7 and the end portion of the EDX device 12, it is possible to provide the collimator 13 which is capable of making the detection efficiency of the EDX device 12 maximum and also of holding the entrance of the scattering electrons into the collimator 13 to a minimum while maintaining the detection efficiency as it is.

While the example has been described in which the EDX detector 11 is mounted to the scanning electron microscope to which the objective lens of the magnetic field leakage type is attached it should be noted that even when the EDX spectrometer 11 is mounted to the scanning electron microscope to which the objective lens of the inlens type is attached, the same effects can be obtained.

As set forth hereinabove, according to the present invention, since the X-rays can be detected efficiently by removing the scattering electrons which have been emitted from the sample without influencing the magnetic field generated by the objective lens, in the X-ray analysis in which the EDX spectrometer is combined with the high resolution scanning electron microscope having the sample arranged in the magnetic field of the objective lens, the effect that it is possible to perform the X-ray analysis at high sensitivity without injuring the resolution of the scanning electron microscope.

We claim:

1. An energy dispersive X-ray analyzer including means for emitting electron beams, a condenser lens for condensing the electron beams, a magnetic field type objective lens, and an energy dispersive X-ray spectrometer, the X-rays which have been emitted from a sample arranged in a leakage magnetic field of said magnetic field type objective lens by irradiation of electrons being detected by said energy dispersive X-ray detector, wherein a collimator which is made of a non-magnetic material and an inner wall of which has an irregular structure is provided between said energy dispersive X-ray spectrometer and the sample.

2. An energy dispersive X-ray analyzer according to claim 1, wherein at least part of said collimator is located in the leakage magnetic field of said magnetic field type objective lens.

3. An energy dispersive X-ray analyzer according to claim 1, wherein said collimator is made of a material from which only a smaller number of secondary electrons are emitted by the irradiation of the electrons.

4. An energy dispersive X-ray analyzer according to claim 1, wherein said collimator is sharpened towards the sample.

5. An energy dispersive X-ray analyzer according to claim 1, wherein said collimator is made of a material having a small transmission factor for X-rays.

6. An energy dispersive X-ray analyzer including means for emitting electron beams, a condenser lens for condensing the electron beams, a magnetic field type objective lens, and an energy dispersive X-ray spectrometer, the X-rays which have been emitted from a sample arranged in a leakage magnetic field of said magnetic field type objective lens by irradiation of electrons being detected by said energy dispersive X-ray spectrometer, wherein a collimator which is made of a non-magnetic material and has an opening portion, which is smaller than an opening portion provided on the side of said energy dispersive X-ray spectrometer, and having an inner wall with an irregular structure, is provided between said energy dispersive X-ray spectrometer and the sample.

7. An energy dispersive X-ray analyzer including an electron source, a condenser lens for condensing electron beams emitted from said electron source, an objective lens and a detector for detecting X-rays emitted by an irradiation of a sample with said electron beams which have gone through said objective lens, wherein a collimator is situated between said detector and said sample, and said collimator has at least two materials selected respectively from a non-magnetic material and a material which suppresses transmission of X-rays, and an inner wall of said collimator has a non-magnetic material and is formed in an irregular structure.

8. An energy dispersive X-ray analyzer according to claim 7, wherein at least a part of said collimator situated between said detector and said sample is arranged within a leakage magnetic field of said objective lens.

9. An energy dispersive X-ray analyzer according to claim 7, wherein said collimator is sharpened toward the sample.

10. An energy dispersive X-ray analyzer according to claim 7, wherein said material which suppresses transmission of X-rays is tantalum (Ta), tungsten (W), gold (Au), platinum (Pt), or lead (Pb).

11. An energy dispersive X-ray analyzer including an electron source, a condenser lens for condensing electron beams emitted form said electron source, an objective lens and a detector for detecting X-rays emitted by an irradiation of said a sample with electron beams which have gone through said objective lens, wherein a collimator is situated between said detector and said sample, and said collimator has at least two materials selected respectively from a non-magnetic material and a material which has a transmission factor for X-rays lower than that of said non-magnetic material, and an inner wall of said collimator has a material which has a transmission factor for X-rays lower than that of said non-magnetic material and is formed in an irregular structure.

* * * * *